(12) United States Patent
Lorenzo et al.

(10) Patent No.: US 10,716,574 B2
(45) Date of Patent: Jul. 21, 2020

(54) ANEURYSM DEVICE AND DELIVERY METHOD

(71) Applicant: DePuy Synthes Products, Inc., Raynham, MA (US)

(72) Inventors: Juan Lorenzo, Raynham, MA (US); Lacey Gorochow, Raynham, MA (US); Ariel Soto Del Valle, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 116 days.

(21) Appl. No.: 15/852,887

(22) Filed: Dec. 22, 2017

(65) Prior Publication Data
US 2019/0192168 A1    Jun. 27, 2019

(51) Int. Cl.
| A61B 17/12 | (2006.01) |
| A61F 2/90 | (2013.01) |
| A61F 2/966 | (2013.01) |
| A61M 25/00 | (2006.01) |

(52) U.S. Cl.
CPC .. *A61B 17/12172* (2013.01); *A61B 17/12031* (2013.01); *A61B 17/12113* (2013.01); *A61F 2/90* (2013.01); *A61B 2017/1205* (2013.01); *A61B 2017/12054* (2013.01); *A61F 2002/9665* (2013.01); *A61M 2025/0042* (2013.01)

(58) Field of Classification Search
CPC .............................. A61B 17/12113; A61F 2/90
See application file for complete search history.

(56) References Cited

U.S. PATENT DOCUMENTS

| 6,391,037 | B1 | 5/2002 | Greenhalgh |
| 6,506,204 | B2 | 1/2003 | Mazzocchi et al. |
| 8,777,974 | B2 | 7/2014 | Amplatz et al. |
| 8,974,512 | B2 | 3/2015 | Aboytes et al. |
| 8,998,947 | B2 | 4/2015 | Aboytes et al. |
| 9,055,948 | B2 | 6/2015 | Jaeger et al. |
| 9,232,992 | B2 | 1/2016 | Heidner et al. |
| 9,314,326 | B2 | 4/2016 | Wallace et al. |
| 2003/0171739 | A1 | 9/2003 | Murphy et al. |
| 2005/0251200 | A1* | 11/2005 | Porter .............. A61B 17/12022 606/200 |
| 2006/0052816 | A1* | 3/2006 | Bates ............... A61B 17/12013 606/200 |

(Continued)

FOREIGN PATENT DOCUMENTS

| CN | 204 683 687 U | 10/2015 |
| WO | 2005117718 A1 | 12/2005 |

(Continued)

OTHER PUBLICATIONS

Extended European Search Report dated May 2, 2019 in corresponding European Application No. 18214052.5.

*Primary Examiner* — Richard G Louis
(74) *Attorney, Agent, or Firm* — Troutman Sanders LLP (57) ABSTRACT

The present disclosure relates to a self-expanding braid for treating an aneurysm. The braid can include a lumen with a proximal end opposite a distal end. Translating the braid can cause a distal segment of the braid to expand and form an outer occlusive sack while a segment proximal the distal segment can invert into the outer occlusive sack like a tube sock. The braid can then be detached from its delivery system.

8 Claims, 9 Drawing Sheets

(56) References Cited

U.S. PATENT DOCUMENTS

| | | |
|---|---|---|
| 2006/0064151 A1 | 3/2006 | Guterman et al. |
| 2008/0281350 A1 | 11/2008 | Sepetka et al. |
| 2010/0023046 A1 | 1/2010 | Heidner et al. |
| 2010/0324649 A1 | 12/2010 | Mattsson et al. |
| 2011/0152993 A1 | 6/2011 | Marchand et al. |
| 2012/0283768 A1 | 11/2012 | Cox et al. |
| 2013/0110066 A1 | 5/2013 | Sharma et al. |
| 2013/0204351 A1 | 8/2013 | Cox et al. |
| 2014/0135812 A1 | 5/2014 | Divino et al. |
| 2014/0200607 A1 | 7/2014 | Sepetka et al. |
| 2015/0209050 A1 | 7/2015 | Aboytes et al. |
| 2015/0272589 A1 | 10/2015 | Lorenzo |
| 2015/0342613 A1 | 12/2015 | Aboytes et al. |
| 2015/0374483 A1* | 12/2015 | Janardhan .............. A61M 29/00 606/200 |
| 2016/0022445 A1 | 1/2016 | Ruvalcaba et al. |
| 2016/0249934 A1* | 9/2016 | Hewitt ............. A61B 17/12031 606/200 |
| 2017/0114350 A1 | 8/2017 | Shimizu et al. |
| 2018/0242979 A1 | 8/2018 | Lorenzo |

FOREIGN PATENT DOCUMENTS

| | | |
|---|---|---|
| WO | 2015160721 A1 | 10/2015 |
| WO | 2015171268 A1 | 11/2015 |

\* cited by examiner

805 — positioning an occlusive device within a microcatheter and in communication with a delivery tube, the occlusive device including a braid capable of expanding and inverting into itself 810 — distally sliding, by the delivery tube, the braid from the microcatheter;

815 — radially expanding, as the braid distally exists the microcatheter, a distal segment of the braid between proximal and distal ends of the braid to form an occlusive sack within the aneurysm 820 — inverting the proximal end of the braid into the occlusive sack 825 — detaching the braid from the delivery tube and withdrawing the delivery tube from the aneurysm

905 — slidably positioning a delivery tube within a microcatheter;

910 — slidably positioning a braid with the delivery tube, the braid being in a collapsed state and comprising a distal end and a proximal end 915 — selectively positioning the microcatheter, the delivery tube, and the braid into the vasculature of the aneurysm;

920 — distally sliding the braid, by the delivery tube, from the microcatheter towards the aneurysm 925 — causing a distal segment between the proximal and distal ends of the braid to move from the collapsed state within the microcatheter to a deployed stated defined by the distal segment radially expanding to form an occlusive sack as the distal end of the braid is moved distally from the microcatheter;

930 — inverting a proximal seng into the occlusive sack; and

935 — releasing the braid within the aneurysm and withdrawing the delivery tube and the microcatheter from the aneurysm.

ANEURYSM DEVICE AND DELIVERY METHOD

FIELD

This disclosure relates to medical instruments, and more particularly, delivery systems for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the brain tissue surrounding cranial vessels the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves.

One particular type of occlusive approach endeavors to deliver and treat the entrance or "neck" of the aneurysm as opposed to the volume of the aneurysm. In such "neck" approaches, by minimizing blood flow across the neck, then a cessation of flow into the aneurysm may be achieved. In turn, a thrombotic mass may naturally form without having to deliver embolic materials, as previously described. This is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches are not without drawbacks. It is desired to block the neck of the aneurysm in the parent vessel. Further, embolic coils do not always effectively treat aneurysms as re-canalization of the aneurysm and/or coil compaction can occur over time.

The solution of this disclosure resolves these and other issues of the art.

SUMMARY

In some aspects, the present disclosure relates to a self-expanding braid for treating an aneurysm. The braid can include a lumen with a distal end opposite a proximal end. Translating the braid can cause the delivery portion to expand and form an occlusive sack as well as invert and fold into itself thereby for occluding an aneurysm.

In certain embodiments, an occlusive device for treating an aneurysm is provided. The device can include a delivery system and a braid being slideably disposed within the microcatheter in a collapsed state. The braid can have a distal end opposite a proximal end. The braid can include a distal segment between the distal and proximal ends. The braid can be distally translatable from within the microcatheter to a deployed state. The braid can expand to the deployed state as the distal end of the braid exits the microcatheter causing the distal segment to radially expand to form an occlusive sack for the aneurysm.

In some embodiments, the distal segment is capable of being disposed across the aneurysm neck, wherein the distal segment can include a porosity reduced relative to the occlusive sack thereby deflecting, diverting, and/or slowing a flow into the aneurysm.

In some embodiments, the distal segment is capable of being disposed across the aneurysm neck, wherein the distal segment can include a higher braid angle relative to the occlusive sack.

In some embodiments, distally translating the braid after the occlusive sack is formed causes one or more segments proximal the distal segment to invert and tuck into the occlusive sack. In some embodiments, wherein the one or more segments proximal the distal segment have an increased braid angle relative to a braid angle of the distal segment to facilitate inversion. In some embodiments, in the deployed state, the braid is detachable from the delivery system in the aneurysm. The delivery system can also include a delivery tube with a distal end and a proximal end. The distal end of the delivery tube can be detachably connected to the proximal end of the braid whereby the delivery tube can be translatably disposable within a microcatheter. The delivery tube can distally translate the braid within the microcatheter from the collapsed state to the deployed state.

In some embodiments, the braid can include a tapered segment disposed between the distal segment and a proximal segment that can be elongate (e.g., partially, substantially, and/or entirely). The tapered segment can have a tapered shape. The proximal segment can be disposed on or adjacent the proximal end of the braid. The occlusive sack of the distal segment can be spherical or any other shape adequate to occlude the aneurysm when in the deployed, expanded state. The distal segment can form into the occlusive sack of the braid, which can be located at the neck of the aneurysm, by having the distal segment remain in place in the aneurysm, and the proximal segment translating distally, eventually inverting into the distal segment. The occlusive sack can be capable of sealing the neck of the aneurysm. In some embodiments, the tapered segment is operable to cover the neck of the aneurysm and the proximal segment can be operable to tuck into the occlusive sack formed by the distal segment. The tapered segment can divert flow or reduce the velocity of flow into the aneurysm. The proximal segment can attach the braid to the distal end of the delivery tube and, after the distal segment has expanded to form the occlusive sack, can initiate inversion of the proximal end of the braid into the occlusive sack of the distal segment. In one embodiment, inverting the proximal end functions such as a tube sock into the distal segment.

In some embodiments, the occlusive sack of the distal segment can be a collapsible cage-like vaso-occlusive structure. In some embodiment, the braid can include one or more buckle portions defined between the distal segment and the tapered and/or proximal segments. In this regard, the proximal end of the braid overlaid internal to the occlusive sack of the distal segment can be formed by inverting at the buckle portion, as the braid continues distally translating from the microcatheter and after the occlusive sack of the distal segment is formed by radial expansion. The distal segment can also include fewer wire segments than the tapered and proximal segments.

In some embodiments, each of the distal, tapered, and proximal segments can include different braid properties.

In some embodiments, the tapered segment diverts flow as the distal segment forms the occlusive sack adjacent or is against a wall of the aneurysm and the proximal segment inverts into the distal segment at the neck of the aneurysm.

In some embodiments, an imaging device operatively is in communication with the occlusive device, wherein the imaging device is capable of imaging the sack with respect to the aneurysm. An orientation of the occlusive sack can be adjustable by the braid being distally or proximally moved.

In some embodiments, a braid for treating an aneurysm is provided. The braid can have a distal segment defined between proximal and distal ends of the braid. The braid can also have a tapered segment disposed between the distal segment and an proximal segment. The proximal segment can be disposed on or adjacent the proximal end. The braid can be capable of moving from a collapsed state within a microcatheter to a deployed state external to the microcatheter. In this embodiment, translating the braid so the distal end is distal of the microcatheter causes the distal segment to radially expand and form an outer occlusive sack. The occlusive sack can have a diameter greater than a diameter of the microcatheter. Additionally, translating the braid distally after the outer occlusive sack is formed can cause the tapered segment to invert into the occlusive sack.

In some embodiments, the braid can be detachably deployable by a delivery system to an aneurysm. The lumen of the braid can also include a buckle portion disposed between the distal segment and the tapered and/or proximal segments. The buckle portion can cause the tapered segment to invert into the occlusive sack. In some embodiments, a braid angle of the tapered segment can be adjusted (e.g., increased) compared to a braid angle of the distal segment.

In some embodiments, a method of delivering an occlusive device to an aneurysm in a blood vessel in a patient is disclosed. The method can include slidably positioning a delivery tube within a microcatheter; slidably positioning a braid with the delivery tube, the braid being in a collapsed state and comprising a distal end and a proximal end; selectively positioning the microcatheter, the delivery tube, and the braid into vasculature of the aneurysm; distally sliding the braid, by the delivery tube, from the microcatheter towards the aneurysm; causing a distal segment between the proximal and distal ends of the braid to move from the collapsed state within the microcatheter to a deployed stated defined by the distal segment radially expanding to form an occlusive sack as the distal end of the braid is moved distally from the microcatheter; inverting a segment proximal the distal segment into the occlusive sack; and releasing the braid within the aneurysm and withdrawing the delivery tube and the microcatheter from the aneurysm.

In some embodiments, the inverting the segment proximal the distal segment into the occlusive sack can deflect, divert, and/or slow a flow into the aneurysm.

In some embodiments, the method can include imaging the occlusive sack of the braid with respect to the aneurysm; determining whether the aneurysm is occluded by the sack; and distally or proximally sliding the braid to adjust the sack and to occlude the aneurysm.

In some embodiments, the method can include adjusting (e.g., increasing) a braid angle of the proximal segment; positioning said segment adjacent or in communication with a neck of the aneurysm; and deflecting, diverting, and/or slowing a flow into the aneurysm when the proximal segment is inverted into the occlusive sack.

In some embodiments, the method can include sealing, by the occlusive sack, the neck of the aneurysm.

In some embodiments, the method can include positioning the distal segment across a neck of the aneurysm; and reducing the porosity of the distal segment relative to the occlusive sack.

In some embodiments, the method can include positioning the distal segment across a neck of the aneurysm; and rendering higher a braid angle relative to the occlusive sack.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Figure 1:
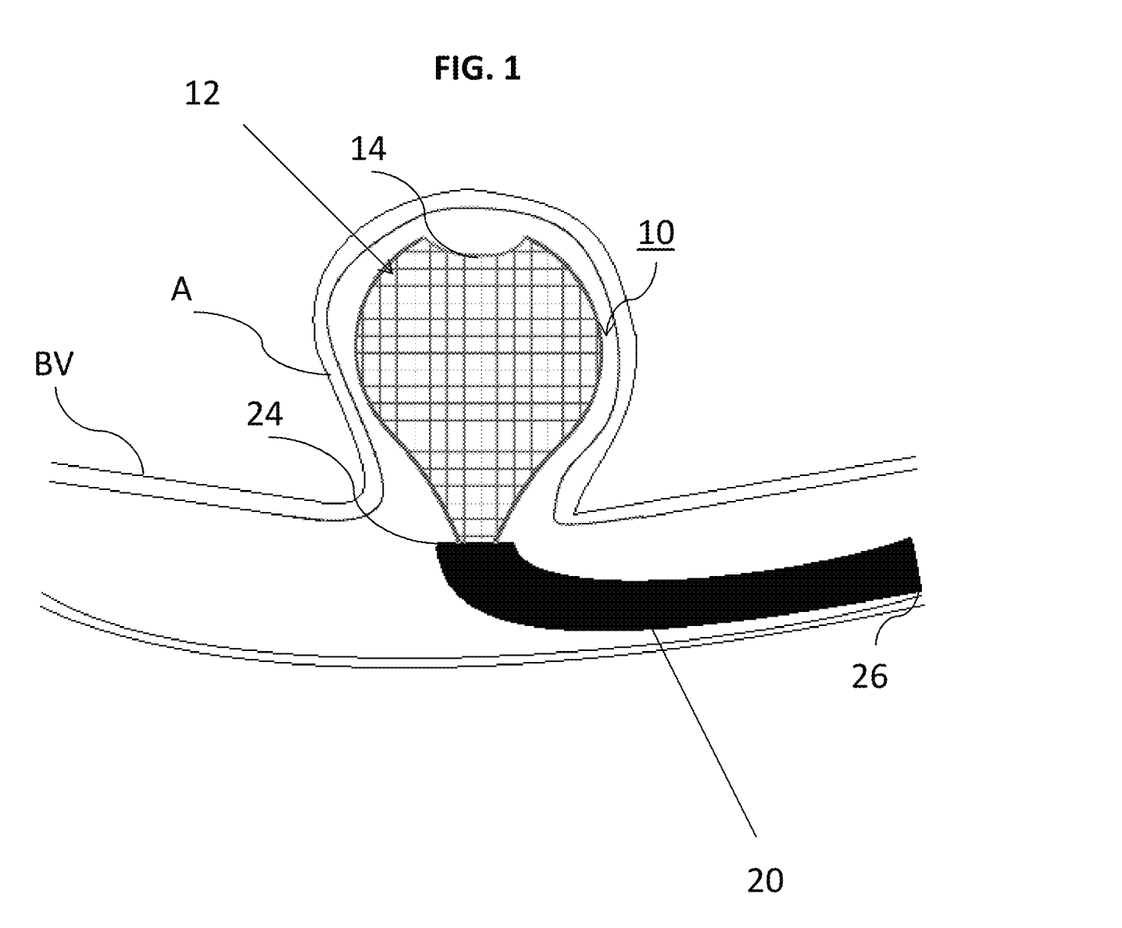
FIG. 1 depicts an example occlusive device of this disclosure deployed into an aneurysm.

The occlusive device 1 and corresponding delivery system 40 disclosed here addresses the drawbacks of previous approaches. Turning to FIG. 1, an example occlusive device 1 of this disclosure is shown deployed into an aneurysm A of blood vessel BV but not yet released from delivery system 40. The delivery system 40 can include a microcatheter 20 with a delivery tube 30 slideably disposed therein. In FIG. 1, the microcatheter 20 has been delivered to the aneurysm A and an occlusive sack formed by distal segment 12 of braid 10 is shown forming a predetermined shape and structure that outlines and supports the walls of the aneurysm A so as to occlude aneurysm A. Segment 12 can be formed on, with, or otherwise about distal end 14 of braid 10. The microcatheter 20 size is selected in consideration of the size, shape, and directionality of the aneurysm or the body lumens the catheter must pass through to get to the treatment site. The microcatheter 20 may have a total usable length anywhere from 80 centimeters to 170 centimeters. The microcatheter 20 may have an inner diameter ID of anywhere between 0.015 and 0.032 inches. The outer diameter OD may also range in size and may narrow at either its proximal end or distal end. At its proximal end 26, the microcatheter 20 may be attached to another device, and at its distal end 24 may be operable to positioned at the neck of the aneurysm A. While the distal end 24 of the microcatheter 20 as shown contains the braid 10, the end 24 may be varied in shape and may curve at an angle.

Figure 2:
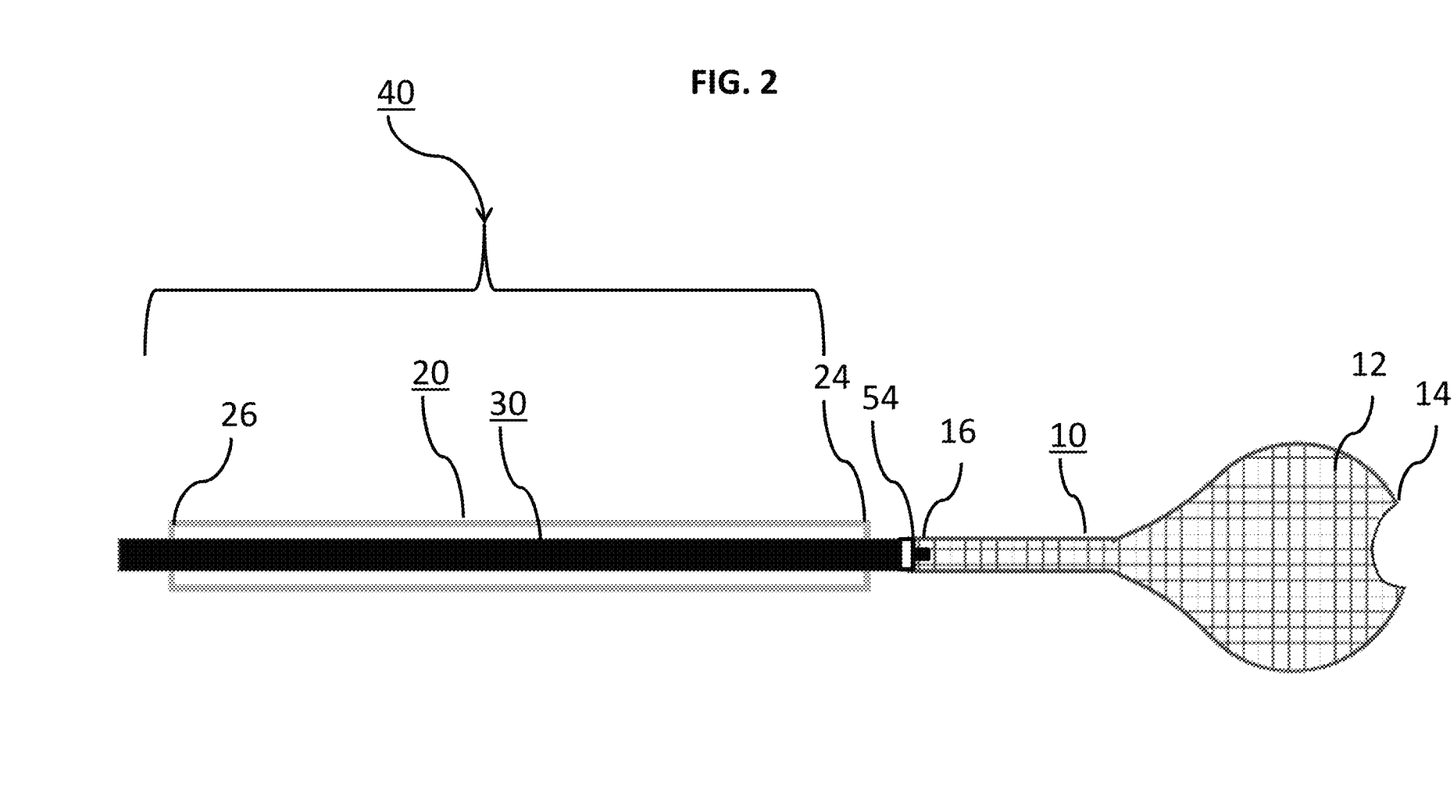
FIG. 2 is a schematic side view of an exemplary delivery system with an occlusive device in communication within a microcatheter.

Turning to FIG. 2, a schematic side view of braid 10 and delivery system 40 is shown in a deployed configuration but prior to being positioned in a location of interest in the vasculature. System 40 can include a delivery tube 30 and a microcatheter 20. The delivery tube 30 can be capable of being distally pushed from a microcatheter 20 and the delivery tube 30 can have an inner lumen. Delivery tube 30 can be substantially elongate and can extend from the proximal 26 to the distal end 24 of microcatheter 20. Tube 30 can generally run along the inner lumen of microcatheter 20 and may leave a space between its outer surface and the internal surface of microcatheter 20. In turn, delivery tube 30 and microcatheter 20 may be axially aligned. System 40 can deliver braid 10 to a location of interest (e.g. a lesion site) using microcatheter 20. In certain embodiments, microcatheter 20 can be pre-placed at a level of the aneurysm neck and used to track the device 1 to the lesion. Delivery tube 30 can be in mechanical connection with braid 10 at locking portion 54. Braid 10 may be attached to locking portion 54 by slidable attachment, permanent attachment (e.g. crimped, laser, ultrasonic weld, or other sources of heat, adhesive, or the like) or other detachable attachment approaches. When delivery tube 30 is mechanically attached to braid 10 at locking portion 54, distally translating, sliding, or otherwise moving tube 30 towards the aneurysm A can cause braid 10 to begin moving from a collapsed condition within microcatheter 20 to a deployed condition external to microcatheter with occlusive sack of segment 12, as discussed more particularly below.

The inner lumen of braid 10 can include a distal end 14 and a proximal end 16. The distal end 14 can be opened and/or be capable of allowing for sizing or conforming to the aneurysm A. For example, if the aneurysm is relatively small, distal end 14 may be a closed end, whereas in a larger aneurysm the same braid 10 can have an open distal end 14. The inner lumen of braid 10 can be formed from a self-expanding and an invertible multi-filament outer surface that can includes a mesh. The occlusive sack of braid 10 can be formed during deployment as distal end 14 of braid 10 slides out and exits microcatheter 20. The mesh of braid 10 can be defined by one or more mesh patterns with mesh openings defined by braided filaments. For example, the mesh of braid 10 can include a porosity region associated with the occlusive sack formed by braid 10. The mesh of braid 10 can be comprised of a tube of mesh, closed at one end (e.g. proximal end 16) and be made of several materials such as deposited thin films. The self-expanding mesh of braid 10 can include multiple wires, for example from 4 to 96 wires. The number of wires can be a factor in controlling material properties of the braid 10, including the stiffness.

The occlusive sack of braid 10 can be formed by braid 10 being distally translated from a collapsed state within microcatheter 20 and attached to delivery tube 30. The mesh of braid 10 is configured so that as braid 10 is distally translated and its end 14 exits from within microcatheter 20, segment 12 will begin immediately expanding. As braid 10 is further translated, the segments of braid 10, including segment 12 and its corresponding occlusive sack, will take shape. Fewer wires of the mesh of braid 10 can be used as a whole. The wires can be made from multiple alloys such as a nickel-titanium alloy, cobalt chromium alloys, Platinum, Nitinol, Stainless Steel, Tantalum, or other alloys, or any other suitable biocompatible materials, or combination of these materials. Also, these materials can be absorbable or non-absorbable by the patient over time.

The apertures in the mesh of braid 10 can also create a substantially unitary frame work or mesh. Thus, the apertures may be of any size, shape, or porosity, and may be uniformly or randomly spaced throughout the wall of the mesh of braid 10. The apertures can provide the tubular element of braid 10 with flexibility and also assist in the transformation of the mesh from the collapsed state to the expanded, deployed state, and vice versa.

Figure 3:
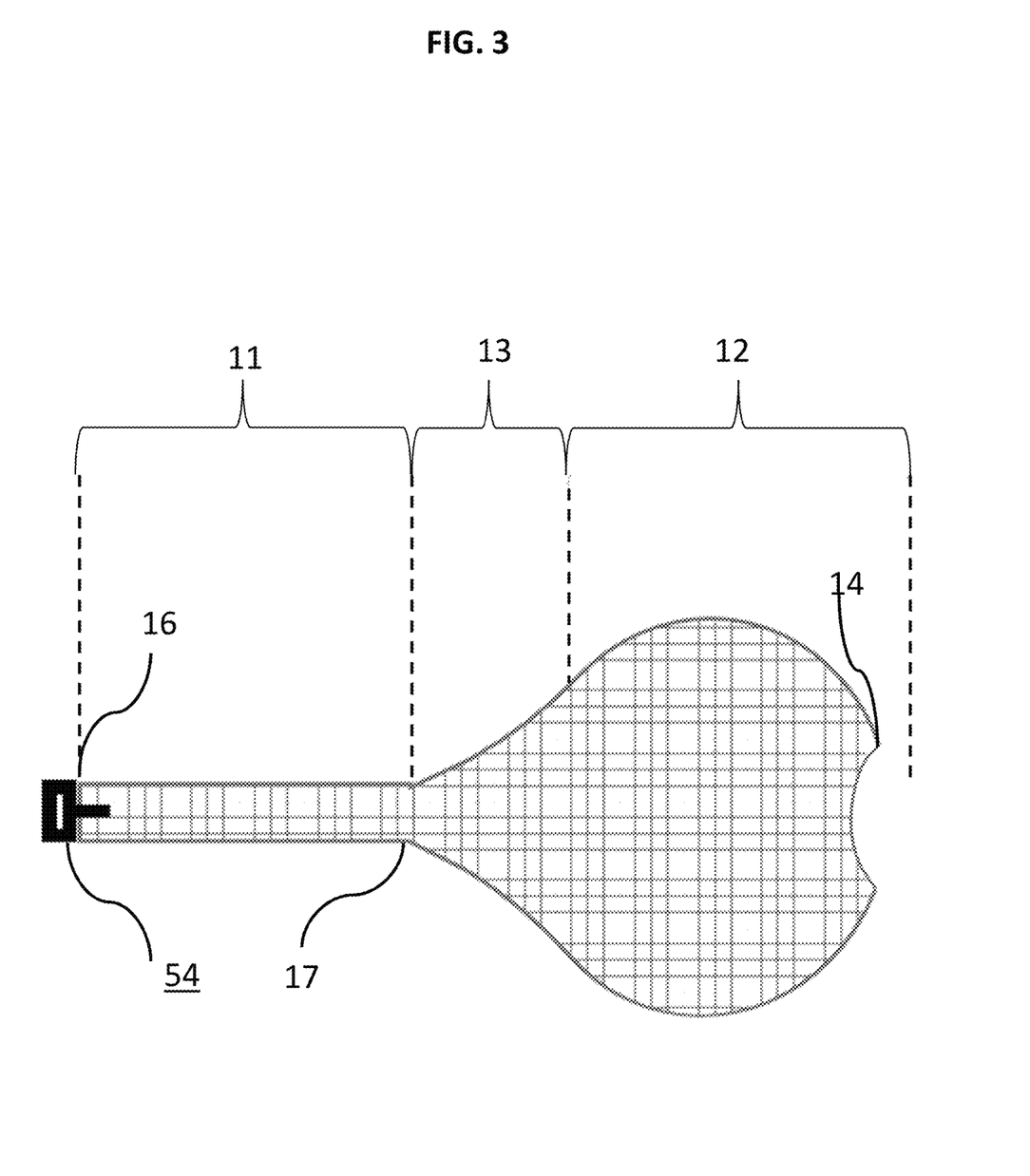
FIG. 3 is an enlarged schematic side view of the braid of FIGS. 1-2 in an expanded state.

Turning to FIG. 3, an enlarged schematic side view of the braid 10 of FIGS. 1-2 is shown in a close-up, expanded state. Other portions of the mesh of braid 10 can have different porosities and/or other material properties, including segments 11 and 13 of braid 10. The braid 10 can include several segments, including a generally spherical shaped segment associated with sack 12 along with a proximal tapered cone segment 13 leading to a relatively elongate proximal segment 11. Segment 11 of the braid 10 can have porosity less than the porosity of segment 13 and/or the segment of sack 12. The porosities associated with segments 11, 12, 13 and/or any other region or segment of braid 10 include filaments having modified braid angles at the different respective regions. For example, the braid angle can be modified by removing filaments in the respective region or by adding a coating or covering to a respective region or by selectively modifying the cross section of the wires. Portions of braid 10 on or proximate end 16 may be more pliable that portions of braid 10 on or proximate end 14 in order to induce self-expansion during delivery and inversion as braid 10 forms its predetermined, sack-like shape within aneurysm A (see, e.g., segment 12). The outer surface of braid 10 can also be made from nitinol with interwoven platinum filaments for radiopacity. The tapered segment 13 adjacent to the spherical segment 12 can allow the braid 10 to invert on itself (like a sock) as the device 1 is fully deployed in the aneurysm A. To facilitate inversion of the braid 10 in the segment 13, the braid 10 can be modified to weaken or make it more likely to invert. For example, segment 13 can include a buckle portion 17 that includes a localized braid angle change, removal of wire segments, localized heat treatment, and other approaches to change braid properties. In certain embodiments, the braid angle of segment 13 can be increased relative to other portions of braid 10 so that the porosity of braid 10 across the neck is reduced so that a flow into the aneurysm is deflected, diverted, or slowed. This is because segment 13 can be in communication with the neck of the aneurysm when braid 10 is inverted and deployed in the aneurysm, since end 16 can be tucked into segment 12 (e.g., see FIG. 5B).

In certain embodiments, a braid angle of one or some of the segments 11, 12, 13 of braid 10 can vary from the longitudinal axis of the braid 10. The wire diameter, pick count (i.e. the number of wire crossovers per lineal measurement) of braid 10 can also vary or otherwise be modified between segments of braid 10 to change the device characteristics. The shape of braid 10 and any of its respective segments can also be heat set. The fibers of braid 10 can be formed by being fastened at their free ends by heat bonding by laser or ultrasonic weld, solvent or adhesive binding, crimping, or any other attachment means. The fibers of each segment of braid 10 may be bonded at their internal crossover points by solvent, adhesive, or heat bonding like laser, ultrasonic weld, or any other source of heat. However, braid 10 is not so limited and it can have a braid angle, pitch count, wire diameter, porosity or any other property of braid 10 that is substantially similar throughout.

FIGS. 4A to 5B depict an enlarged schematic side view of the delivery system 40 and braid 10 as the braid 10 is being pushed into an example aneurysm A. The mesh of braid 10 expands and then proximal end 16 inverts into braid 10 as the occlusive sack of segment 12 of braid 10 is formed. This means that braid 10 inverts along segment 11 in and rests inside of the aneurysm sack once deployed. In one example, the inversion of the mesh of braid 10 can be formed when the end 14 of the braid 10 is relatively fixed against the wall of aneurysm A while end 16 is distally pushed forward away from microcatheter 20 and tucked into the sack of segment 12. In certain embodiments, proximal end 16 of braid 10 can begin inverting as the braid 10 moves distally forward as shown in FIG. 4B and braid 10 does not need for the entire length of 10 to be deployed before the braid starts inverting. In other embodiments, once the entire length of braid 10 is deployed and distal of microcatheter 20, the proximal end 16 can invert and tuck into segment 12. Regardless, in the deployed state, once selectively positioned and arranged in the proper deployed configuration with respect to aneurysm A, braid 10 can be detached. The inversion of braid 10 can be formed akin to a tube sock. In other embodiments, once the mesh of braid 10 is fully deployed and the occlusive sack of braid 10 is formed within aneurysm A, both the ends 14, 16 can be next to or adjacent each other.

Figure 4A:
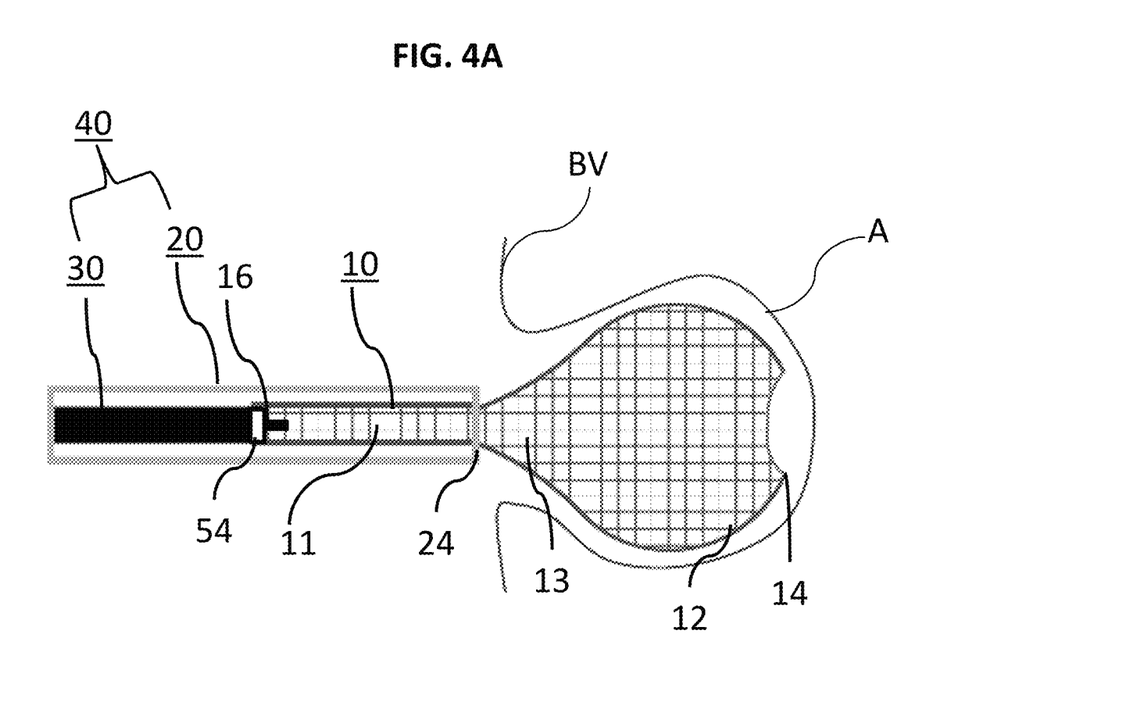
FIG. 4A is an enlarged schematic side view of the delivery system and braid of FIGS. 1-3 as the braid is being pushed into an example aneurysm.

Prior to the arrangement of FIG. 4A, the braid 10 can be assembled with a delivery tube 30 and/or within a microcatheter 20 in a collapsed state. In this respect, the herein disclosed novel delivery system 40 and novel braid 10 can be packaged as a portable kit or system. The assembly between microcatheter 20, delivery tube 30, and/or braid 10 can take place before being introduced into the vasculature. The delivery system 40 used with braid 10, which can include microcatheter 20 and delivery tube 30, can be selectively positioned at the lesion site and delivery tube 30 can begin distally translating braid 10 towards the aneurysm. Braid 10 can expand as or upon its delivery end 14 contacting aneurysm A as it distally moves away from distal end 24 of catheter 20 to form the spherical sack associated with segment 12 within aneurysm A. As shown in FIG. 4A, segment 12 of braid 10 is beginning to take a generally spherical shape internal to aneurysm A as braid 10 contacts dome D of aneurysm A and/or as braid is translated distally deeper into aneurysm A, further away from catheter 20 and tube 30. Delivery tube 30 may also include one or more fasteners operable to securely fasten braid 10 in place prior to deployment.

Figure 4B:
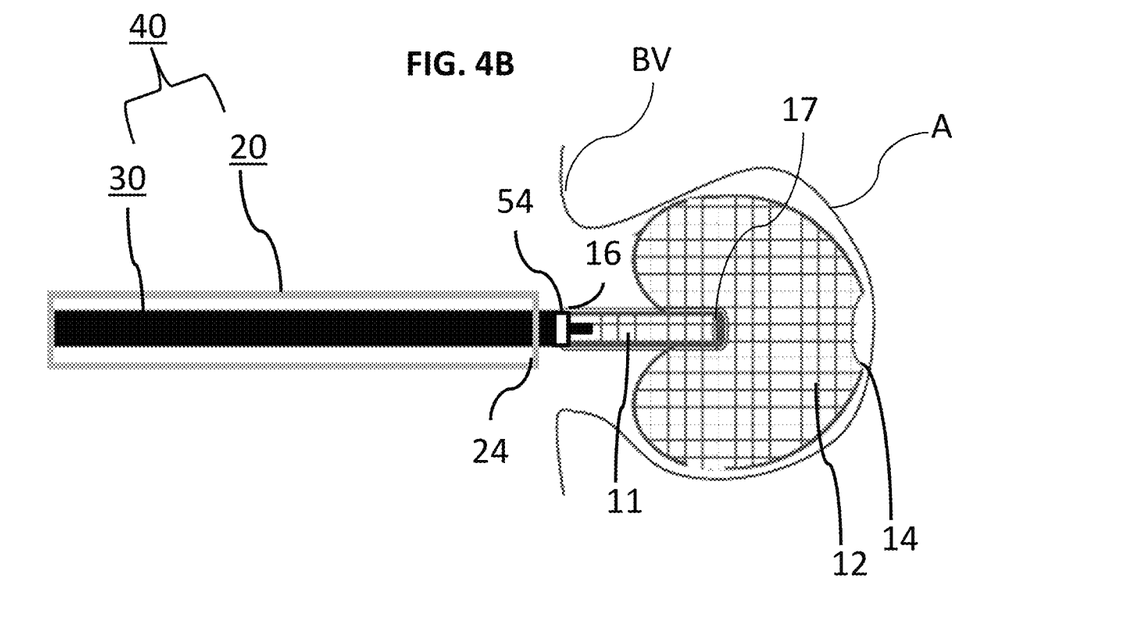
FIG. 4B is an enlarged schematic side view of the delivery system and braid of FIGS. 1-3 as the braid is being pushed into an example aneurysm.

As shown in FIG. 4A, sack 12 can radially expand towards the outer walls of aneurysm A while unexpanded portions (e.g. segment 11) of braid 10 continue to be translated by delivery tube 30. In FIG. 4B, delivery tube 30 distally moves further away from microcatheter 20 and braid 10 begins inverting as its end 16 continues moving distally, by delivery tube 30, away from microcatheter 20 towards aneurysm A. Delivery tube 30 may be driven by a hypotube from its proximal end 36 (not depicted) by an operator or the like. Microcatheter 20 may remain relatively stationary or fixed while delivery tube 30 can be seen distally translating braid 10 towards and through the neck of aneurysm A. Braid 10 can include a pre-weakened or buckle portion 17 so that as braid 10 and delivery tube 30 are distally translated away from microcatheter 20 and into aneurysm A, segment 11 can be translated causing radial expansion of segment 12 to form the corresponding occlusive sack. Continued distal translation of braid 10 can also cause the braid 10 to buckle and for end 16 to invert into sack of segment 12. In certain embodiments, portion 17 can initiate inversion of end 16 into segment 12. Inverting end 16 into segment 12 is particularly advantageous as it prevents braid 10 from creating a protrusion that would otherwise extend into the parent vessel. Instead, any such protrusion is now inverted and tucked into segment 12. Arranging braid 10 in this manner across the neck of the aneurysm, including by inverting end 16 into the sack of segment 12, a flow diversion is created essentially inside of the sack of segment 12.

It is understood that buckle portion 17 may be formed into the interstices of braid 10 between end 14 of braid 10 and locking portion 54 between braid 10 and delivery tube 30 so that inversion occurs after braid 10 has distally translated a predetermined distance outside of delivery tube 30. Portion 17 may be simply a weak point or buckling point pre-set for a particular sack 12 so that buckling is induced so as to avoid strain of aneurysm A. Alternatively, no buckle portion 17 may be included and instead braid 10 may invert and fold into itself upon end 14 of braid contacting the dome D of aneurism A (e.g. based on pre-selected pliability of braid 10).

Figure 5A:
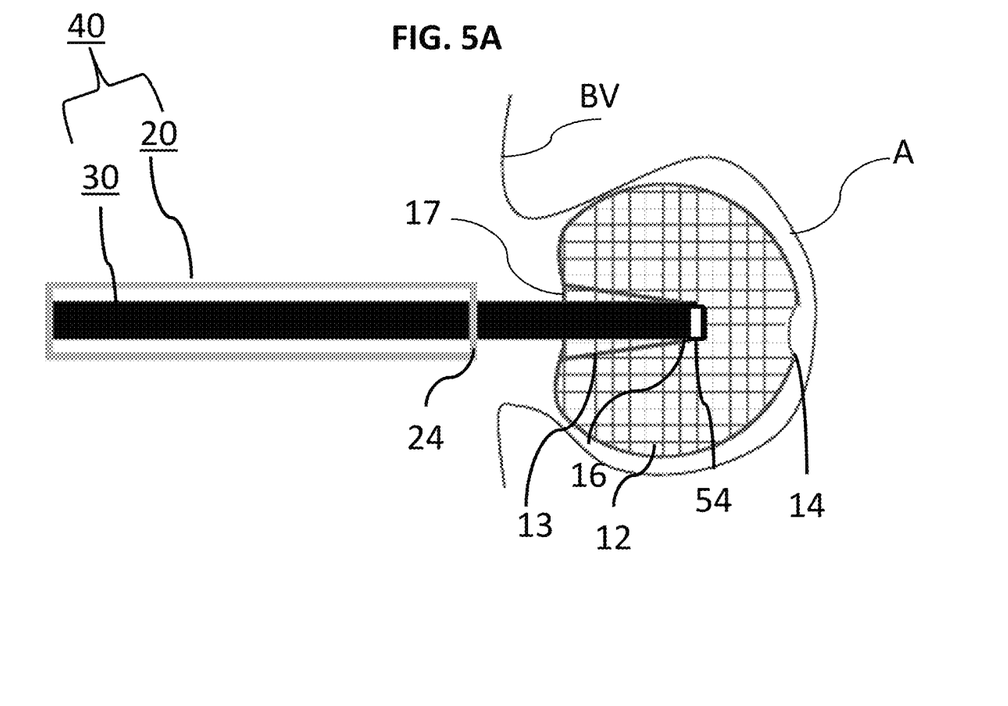
FIG. 5A is an enlarged schematic side view of the delivery system and braid of FIGS. 1-3 as the braid is being pushed into an example aneurysm.
Figure 5B:
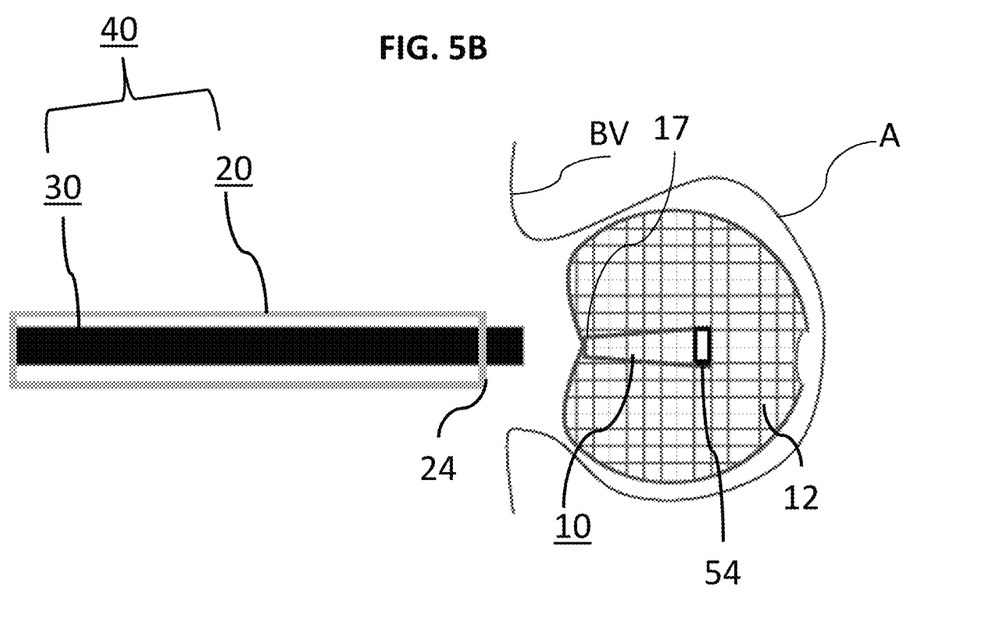
FIG. 5B is an enlarged schematic side view of the delivery system and braid of FIGS. 1-3 after the braid is deployed into an example aneurysm.

Locking portion 54, and/or portions of delivery tube 30 can be at the level of the neck of the aneurysm A as seen under fluoroscopy. In moving between FIGS. 4A-5B, the outer diameter of the braid 10 about segment 12 radially expands to a diameter greater than the microcatheter 20 as the occlusive sack of segment 12 is formed. In FIG. 5A, the delivery system 40 can continue to be distally translated until the junction between end 16 of braid 10, locking portion 54, and delivery tube 30 is fully within the spherical, occlusive sack of segment 12 and inversion of braid 10 stops. Once braid 10, segment 12, and corresponding inversion of end 16 are selectively positioned and arranged to the desired condition (e.g. braid 10 has been translated distally to expand segment 12 to form its sack and segments have been inverted therein), braid 10 can be detached from the delivery tube 30 as shown in FIG. 5B. Delivery tube 30 between FIGS. 4A and 5A continues to distally slide braid 10 until in FIG. 5A, unexpanded, segments aft of segment 12 (e.g. segment 13, segment 11, or any other segments aft of segment 12 not depicted) invert and be tucked into the sack of segment 12. In other words, as the braid 10 is distally translated towards the dome of the aneurysm A, the segments of braid 10 that are proximal of segment 12 can be used to force invert like a tube sock. In turn, delivery tube 30 can be proximally translated back into microcatheter 20 and retracted from the braid 10 and aneurysm A.

The braid wire count of interstices of braid 10 that may form the outer surface of its expandable and invertible mesh can vary depending of the diameter of the sack of segment 12 and/or any sacks inverted internal thereto. For example, in order to induce formation of the predetermined shape and strength of the occlusive sack of segment 12, end 14 of braid 10 may be more pliable than the other end 16, or vice versa, and other segments of braid 10, including segments 11, 12, and 13, may vary from most pliable on or about end 14 and less pliable on or about end 16. Interstices of braid 10 may also form openings for occlusion of the aneurysm.

In FIG. 5B, an example spherical sack of segment 12 fully formed in a manner sufficient to occlude aneurysm A with one or more inverted portions disposed internal to the sack of segment 12, braid 10 can be detached from locking portion 54. However, if the sack of segment 12 is not precisely positioned or if segment 12 and/or any internally disposed segments formed by inversion of segments proximal thereto need to be reset or adjusted within aneurysm A for safe occlusion without risk of rupture, braid 10, including segment 12, can be retracted back into delivery tube 30 by proximally withdrawing delivery tube 30 back into microcatheter 20 while still attached to braid 10. In FIG. 5B, since the sack of segment 12 has been selectively positioned and formed within aneurysm A, braid 10 has been detached from delivery tube 30 and delivery tube 30 and microcatheter 20 can now be retraced from aneurysm A and the lesion site. It is understood that some or all of locking portion 54 can be formed with the microcatheter 20 or delivery tube 30 and/or can be radiopaque so that positioning and detachment can be monitored and/or driven under fluoroscopy.

Figure 6A:
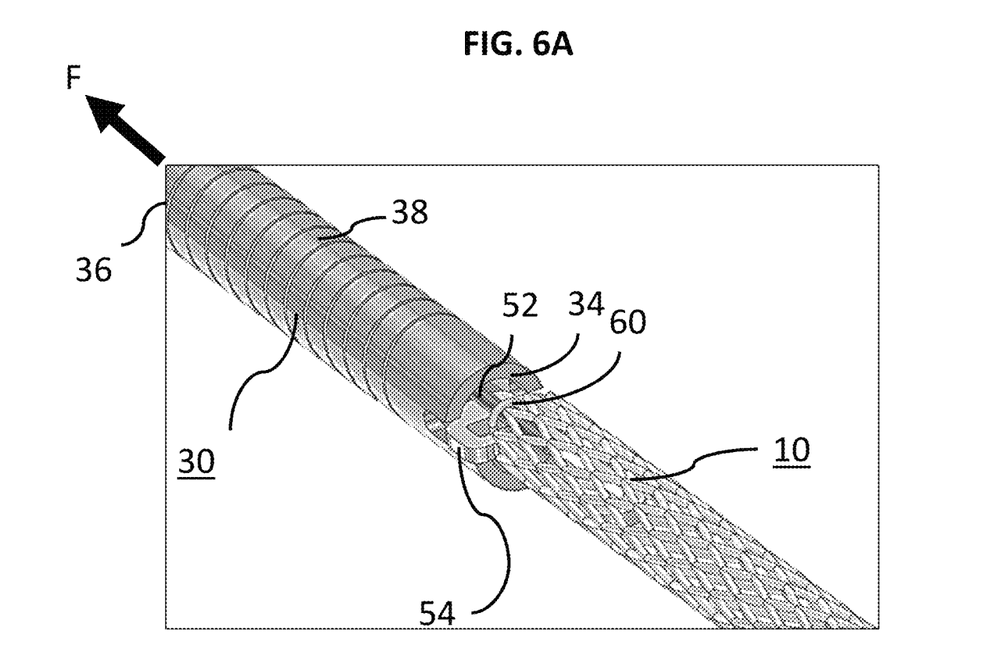
FIG. 6A is a perspective schematic view showing an exemplary delivery system for use with an example occlusive device.

FIGS. 6A to 7B generally illustrate example attachment and delivery between delivery tube 30 and braid 10 for deploying and detaching braid 10 in aneurysm A. The embodiments of FIGS. 6A to 7B is merely one way that delivery tube 30 and braid 10 may be attached at end 34 and any number of attachment means are contemplated as needed or required. The delivery tube 30 as shown can have a lumen extending from a proximal end 36 to a distal, delivery end 34. FIG. 6A illustrates braid 10 engaged with the locking member 52 and loop wire 58 locked into the locking portion 54. The opening 60 of the loop wire 58 can be placed through the locking portion 54. The locking portion 54 preferably takes the form of a small diameter elongate filament, however, other forms such as wires or tubular structures are also suitable. While the locking portion 54 is preferably formed of nitinol, other metals and materials such as stainless steel, PTFE, nylon, ceramic or glass fiber and composites may also be suitable. Locking member 52, in one example, may be an elongated retractable fiber that may extend between ends 24 and 26 of the microcatheter 20. Locking member 52 preferably takes the form of a small diameter elongate filament, however, other forms such as wires or tubular structures are also suitable. While the locking member 52 is preferably formed of nitinol, other metals and materials such as stainless steel, PTFE, nylon, ceramic or glass fiber and composites may also be suitable. When the locking member 52 is put through the opening 60 the braid 10 is now secure. It is understood that delivery tube 30 may include a compressible portion 38 disposed between its ends 34 and 36.

The compressible portion 38 can allow the delivery tube 30 to bend and/or flex. Such flexibility can assist tracking the braid 10 through the microcatheter 20 and the tortuous path through the vasculature. The compressible portion 38 can be formed with interference spiral cuts that can allow for gaps to permit bending but in one example, do not act as a spiral-cut spring. Compressible portion 38 can be axially adjustable between an elongated condition and a compressed condition. However, any other arrangement allowing axial adjustment (e.g., a wound wire or spiral ribbon) can also be suitable for use with detachment systems according to the present disclosure). The compressible portion 38 can be in the elongated condition at rest and automatically or resiliently returns to the elongated condition from a compressed condition, unless otherwise constrained. The function of the compressible portion 38 is described in greater detail herein.

Figure 6B:
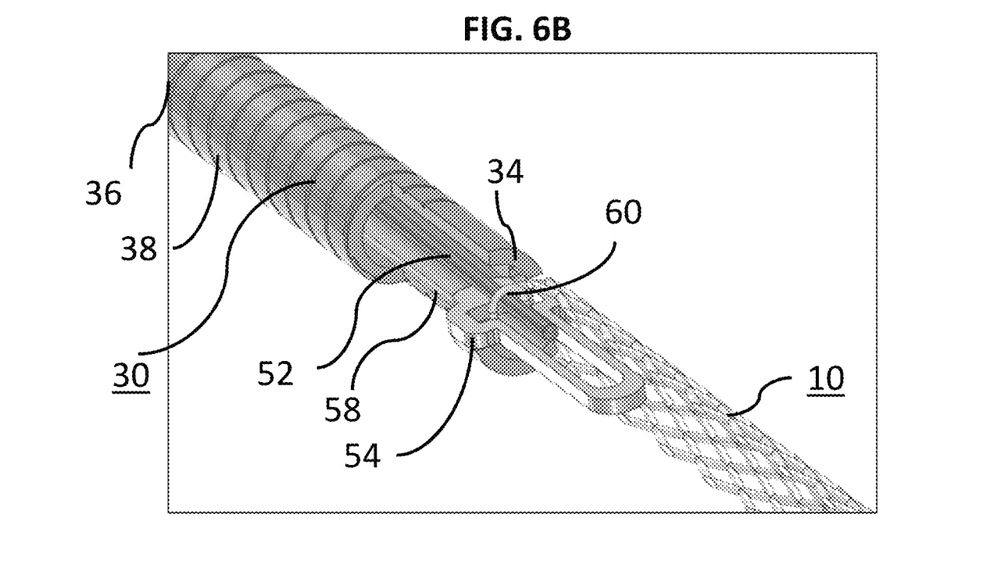
FIG. 6B is a perspective schematic view of FIG. 6A but with partial cross-section of the delivery system and the occlusive device.
Figure 7A:
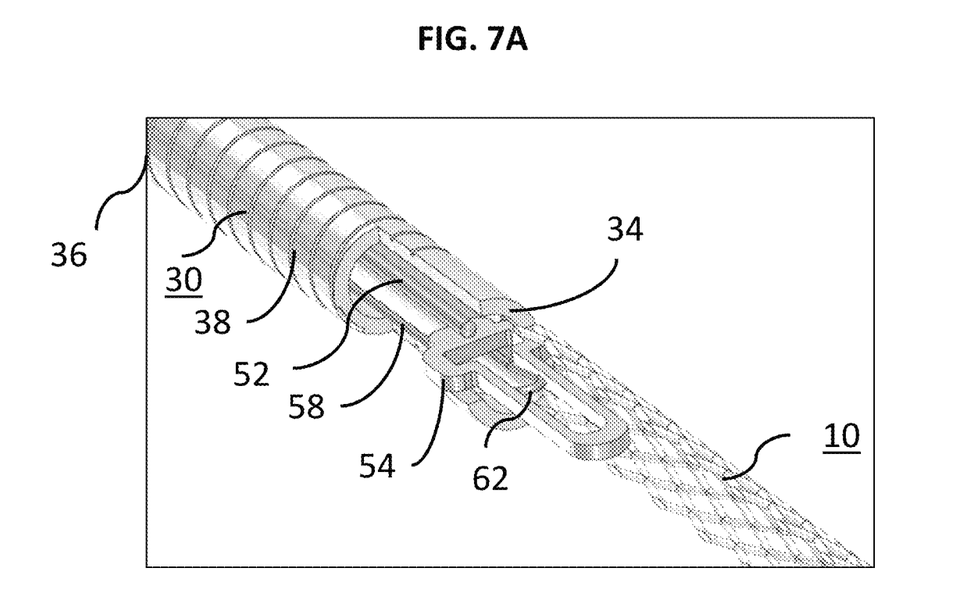
FIG. 7A is a perspective schematic view of FIGS. 6A-6B being deployed with partial cross-section of the delivery system and the occlusive device.
Figure 7B:
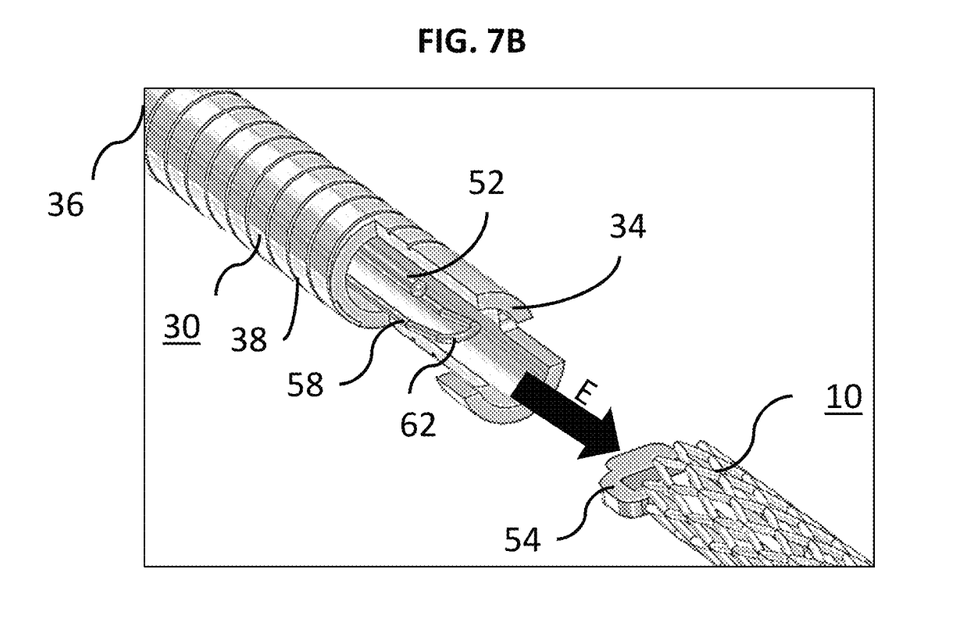
FIG. 7B is a perspective schematic view of FIGS. 6A-6B deployed with the exemplary delivery system detached from the occlusive device.

In FIG. 6A, a force F was previously applied to place the delivery tube 30 in a compressed state. FIG. 6B illustrates the locking member 52 being drawn proximally to begin the release sequence for braid 10. FIG. 7A illustrates the instant the locking member 52 exits the opening 60 and is pulled free of the loop wire 58. The distal end 62 of the loop wire 58 falls away/returns to its preformed shape and exits the locking portion 54. As can be seen, there is now nothing holding the braid 10 to the delivery tube 30. FIG. 7B illustrates the end of the release sequence. Here, the compressible portion 38 of the delivery tube 30 has expanded/ returned to its original shape and "sprung" forward. An elastic force E is imparted by the distal end 34 of the delivery tube 30 to the braid 10 to "push" it away to insure a clean separation and delivery of the braid 10 to the aneurysm A. It is to be understood that the delivery scheme described in FIGS. 6A-7B are merely example approaches to delivery of braid 10.

Figure 8:
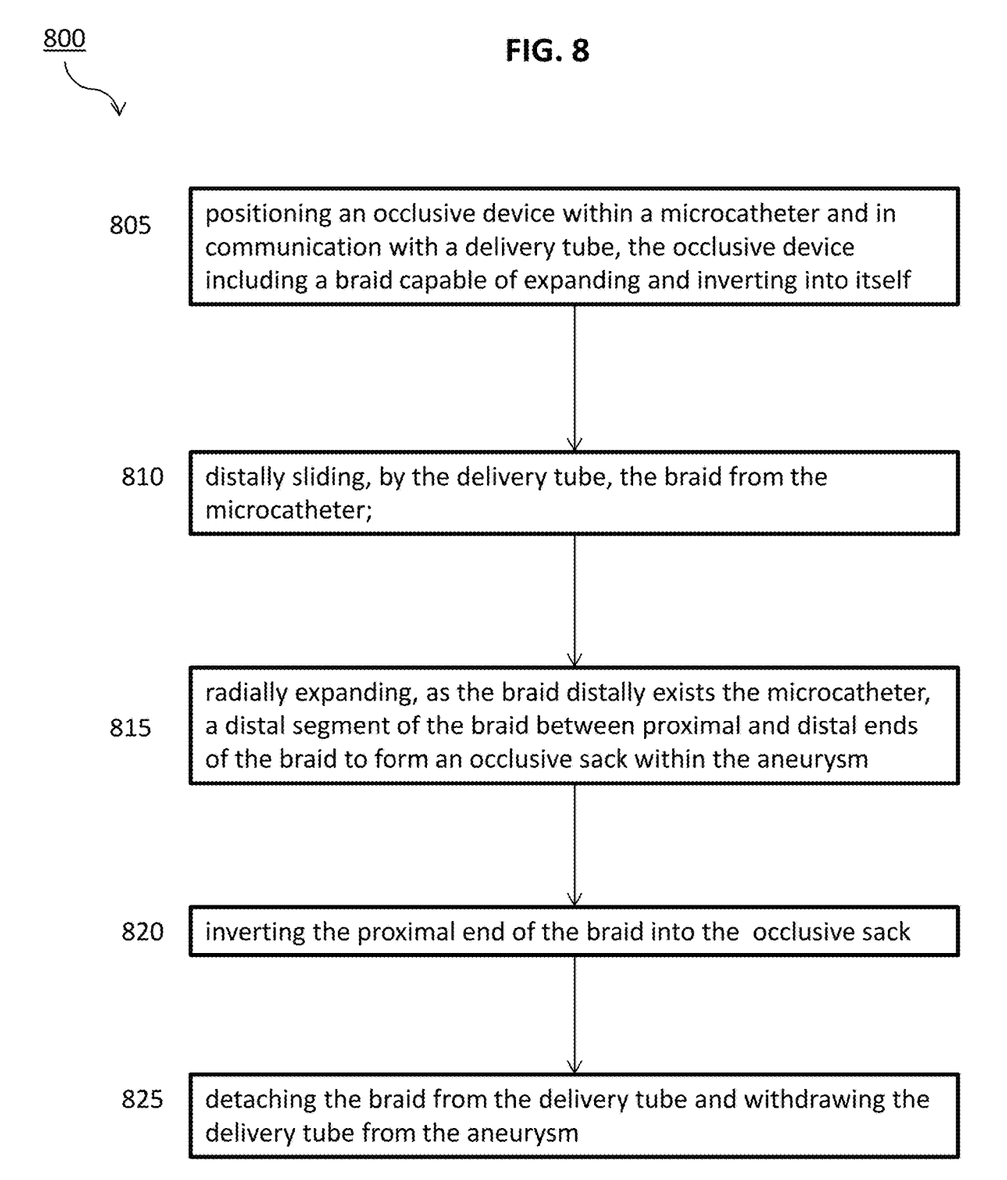
FIG. 8 is a flow diagram for a method of delivering an occlusive device.

FIG. 8 is a flow diagram for a method 800 of delivering an occlusive device. Step 805 includes positioning an occlusive device within a microcatheter and in communication with a delivery tube, the occlusive device including a braid capable of expanding and inverting into itself. Step 810 includes distally sliding, by the delivery tube, the braid from the microcatheter. Step 815 includes radially expanding, as the braid distally exits the microcatheter, a distal segment of the braid between proximal and distal ends of the braid to form an occlusive sack within the aneurysm. Step 820 includes inverting the proximal end of the braid into the occlusive sack. Step 825 includes detaching the braid from the delivery tube and withdrawing the delivery tube from the aneurysm.

Figure 9:
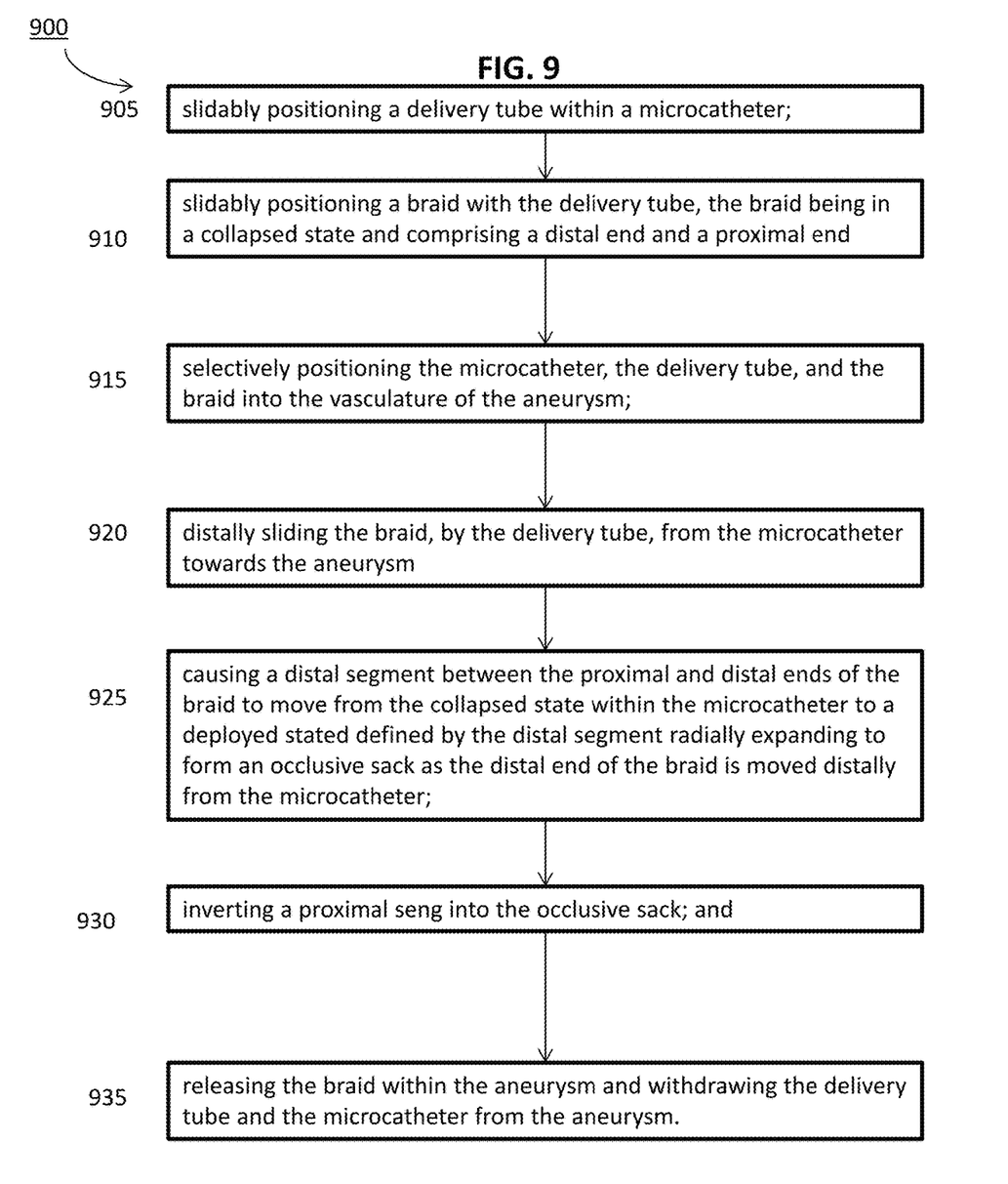
FIG. 9 is a flow diagram for a method of delivering an occlusive device.

FIG. 9 is a flow diagram for a method 900 of delivering an occlusive device. Step 905 includes slidably positioning a delivery tube within a microcatheter. Step 910 includes slidably positioning a braid with the delivery tube, the braid being in a collapsed state and comprising a distal end and a proximal end. This step can also include detachably attaching the proximal end of the braid to the distal end of the delivery tube. Step 915 includes selectively positioning the microcatheter, the delivery tube, and the braid into the vasculature of the aneurysm. Step 920 includes distally sliding the braid, by the delivery tube, from the microcatheter towards the aneurysm. Step 925 includes causing a distal segment between the proximal and distal ends of the braid to move from the collapsed state within the microcatheter to a deployed stated defined by the distal segment radially expanding to form an occlusive sack as the distal end of the braid is moved distally from the microcatheter. Step 930 includes inverting and/or tucking a proximal segment into the occlusive sack. Step 935 includes releasing the braid within the aneurysm and withdrawing the delivery tube and the microcatheter from the aneurysm and the vasculature.

It is understood that variations of the braid 10 can include various materials such as nitinol, stainless steel, bio absorbable materials, and polymers. Braid 10, including any specific portions such as any breaks and corresponding sacks, can be heat set to various configurations such as spherical, oblong, saddle shaped, etc. for the purpose of shaping the initial sack to better match the aneurysm morphology. In addition, the braid 10 can be heat shaped to include weak points to facility the braid buckling once it reaches the dome of the aneurysm. It is also understood that any sack formed by the herein discussed braids 10 can be in a spherical shape as depicted or any other shape, as needed or required, such as ellipsoidal, heart-shaped, ovoid, cylindrical, hemispherical, or the like. Further, interstices of braid 10 that form the sack can vary, or be selectively designed, in size or shape along its length depending on how much braid 10 is caused to radially expand as delivery tube 30 is distally moved.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method of delivering an occlusive device to an aneurysm in a blood vessel in a patient, comprising:
   slidably positioning a delivery tube within a microcatheter;
   slidably positioning a braid with the delivery tube, the braid being in a collapsed state and comprising a distal end and a proximal end;
   selectively positioning the microcatheter, the delivery tube, and the braid into vasculature of the aneurysm;
   distally sliding the braid, by the delivery tube, from the microcatheter towards the aneurysm;
   causing a distal segment between the proximal and distal ends of the braid to move from the collapsed state within the microcatheter to a deployed stated defined by the distal segment radially expanding to form an occlusive sack as the distal end of the braid is moved distally from the microcatheter; then
   inverting and buckling a proximal segment proximal the distal segment into the occlusive sack; and then
   releasing the braid within the aneurysm and withdrawing the delivery tube and the microcatheter from the aneurysm.

2. The method of claim 1, further comprising:
   positioning wherein the distal segment across the aneurysm neck, wherein the distal segment comprises a higher braid angle relative to the occlusive sack.

3. The method of claim 2, further comprising:
   increasing a braid angle of one or more segments proximal the distal segment relative to a braid angle of the distal segment thereby facilitating inversion.

4. The method of claim 1, wherein the distal end of the braid is opened.

5. The method of claim 1, further comprising:
   positioning a tapered segment between the distal segment and the proximal segment; and
   sealing, by the occlusive sack, the neck of the aneurysm.

6. The method of claim 5, further comprising:
   diverting flow, by the tapered segment, as the distal segment forms the occlusive sack adjacent to, or is against, a wall of the aneurysm.

7. The method of claim 1, wherein the occlusive sack of the distal segment is a collapsible cage-like vaso-occlusive structure.

8. The method of claim 1, wherein the distal segment comprises fewer wire segments than the tapered and proximal segments.

* * * * *